United States Patent [19]

Holm

[11] 3,964,475

[45] June 22, 1976

[54] PROTECTING HOSE

[76] Inventor: Anna-Lisa Holm, Prologgatan 14, 42241 Hisings-Backa Goteborg, Sweden

[22] Filed: May 17, 1974

[21] Appl. No.: 471,017

[52] U.S. Cl. ............................. 128/132 R; 128/288; 128/286; 2/DIG. 7; 9/343
[51] Int. Cl.² ........................................ A61F 13/00
[58] Field of Search .......... 128/132, 133, 134, 78 R, 128/87 R, 96, 98, 100, 101, 160, 168, DIG. 20, 287, 288, 518 R, 521, 524, 525; 2/300, DIG. 7; 9/337, 343

[56] References Cited
UNITED STATES PATENTS

| | | | |
|---|---|---|---|
| 689,602 | 12/1901 | Turner | 128/288 |
| 1,093,002 | 4/1914 | Magyar | 9/343 |
| 2,068,998 | 1/1937 | Spanel | 128/288 |
| 2,177,308 | 10/1939 | Spanel | 128/288 |
| 3,043,307 | 7/1962 | Weston | 128/288 |

*Primary Examiner*—Robert W. Michell
*Assistant Examiner*—Henry J. Recla
*Attorney, Agent, or Firm*—Ulle C. Linton

[57] ABSTRACT

A protecting hose preferably for disabled persons is made from a flexible and liquid as well as gas proof material and has the shape of a trouser the legs of which having cuffs adapted to be sealingly arranged around the thighs of the wearer and the waist portion thereof having an inflatable zone, a strap assembly being adapted to hold said inflatable zone pressed against the waist of the wearer.

1 Claim, 4 Drawing Figures

U.S. Patent June 22, 1976 3,964,475
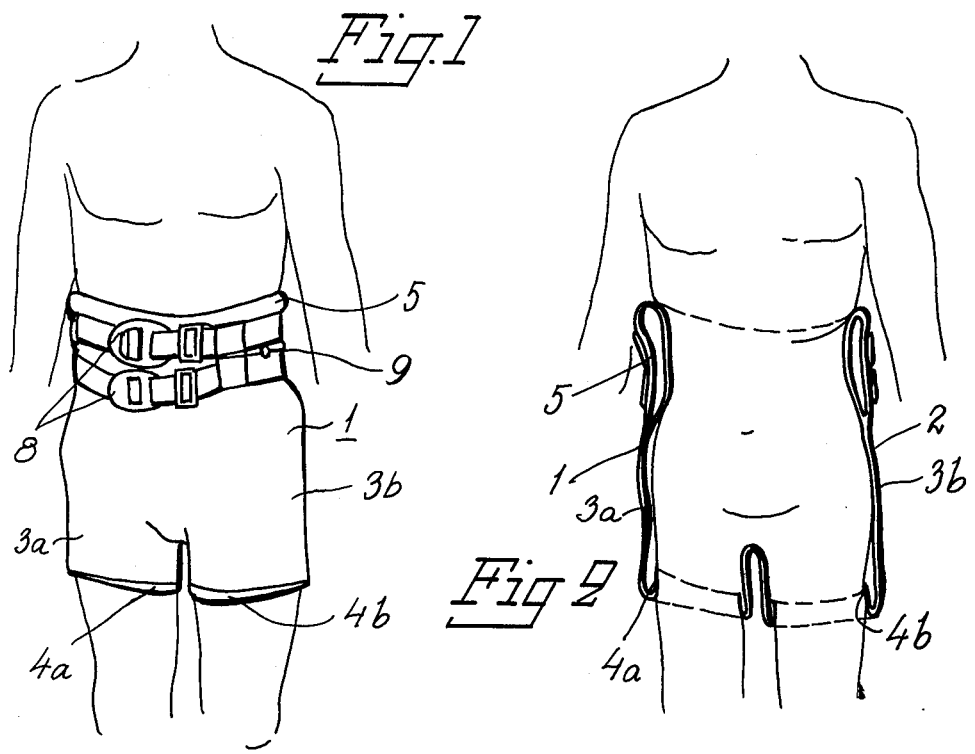
Fig. 1
Fig. 2
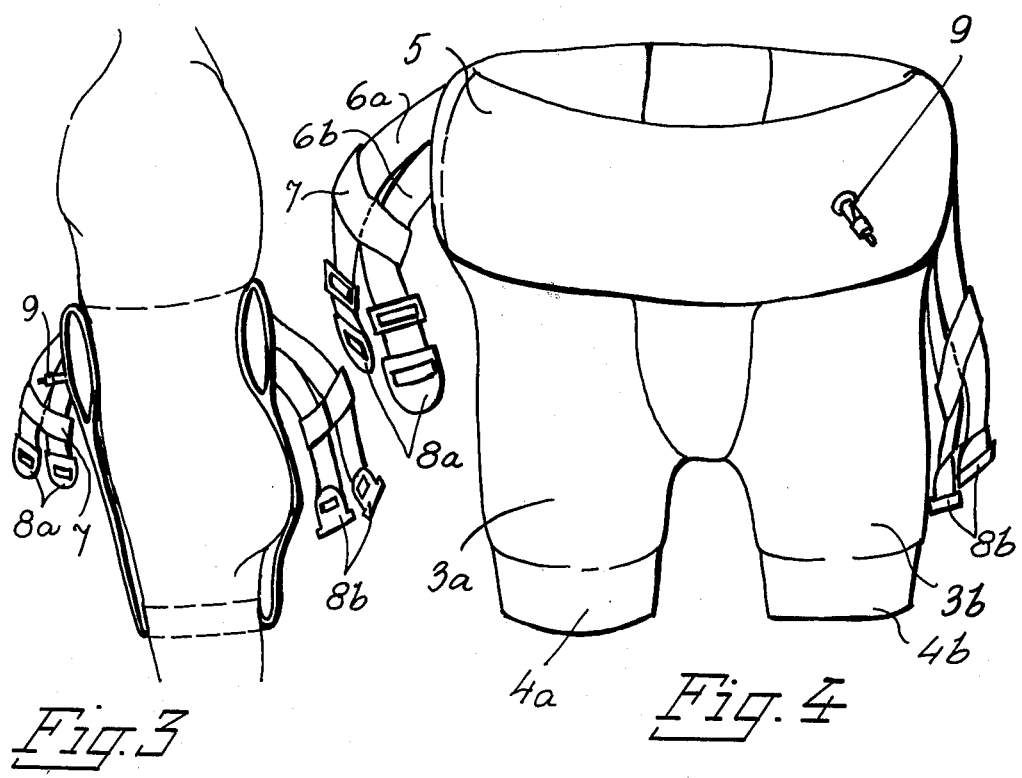
Fig. 3
Fig. 4

PROTECTING HOSE

This invention relates to a protecting hose that primarily is intended to be used by persons which due to inability to control urination and/or relief or because of a great responsibility for infections must isolate their body from the surrounding medium such as water or air. Especially for disabled persons suffering from the problems mentioned above and in spite thereof have to be dwelling in water for example because of the performance of remedial exercises there is a big need of a protecting hose that provides such insulation and furthermore gives a sufficient heat insulation.

To accomplish these and other purposes the invention is carried out according to the claims.

An examplary embodiment of the invention is illustrated in the accompanying drawings, in which FIG. 1 shows the new protecting hose put on a person while FIG. 2 shows the protecting hose in a sectional front view.

FIG. 3 shows a similar section of the protecting hose in a side view and, finally, FIG. 4 shows the protecting hose in the state it assumes before it is put on.

The new protecting hose, that is suitably made from a heat insulating elastically tight-fitting and water and/or gas proof material which contains gas filled cells separated from each other, is generally designated by numeral 1 in the drawing. It comprises a body portion 2 and short trouser legs 3a, 3b. These trouser legs terminate in cuffs or sleeves 4a, 4b made from a thin and pliable material such as rubber so that they in the inwardly folded state thereof according to FIGS. 2 and 3 serve as seals against the thighs of the person wearing the hose. An inflatable rubber ring 5 is attached to the waist portion of the hose for instance by gluing. A strap assembly is attached to the same portion of the hose and comprises two strap parts 6a, 6b positioned at a distance from each other and being kept at the desired distance by means of strap elements 7 or similar attachment means. Co-operating locking means 8a, 8b are provided at the ends of the straps 6a, 6b and the straps are adjustable as to their length in a manner known per se. As can be seen from FIG. 1 and FIG. 3 the rubber ring has a valve 9 for filling of air and said valve is positioned between the separate strap parts 6a, 6b when the hose is put on.

In putting on the protecting hose the waist portion of the hose is somewhat turned inside out in an outward direction and thereafter the hose is put into place and the cuffs 4a, 4b are folded inwardly. When the waist portion has been turned into its correct position the strap assembly is so applicated that the valve 9, mentioned above will be located between the two strap parts 6a, 6b and when the strap assembly is thereafter stretched the rubber ring is inflated so that a perfect seal is obtained.

Naturally, the invention is not limited to the embodiment described above and illustrated in the drawings but may be varied in several ways within the scope of the claims. Thus, it is optional to have the strap assembly attached to the protecting hose or separate from the same and naturally, the strap assembly must not comprise two strap parts separated from each other but only one single strap provided with a special hole for the valve may be utilized as well as it is possible to locate the valve in another way so that the strap may be made without any holes.

I claim:

1. Protecting pants intended to insulate in a water and a gas proof manner a body portion of a person wearing said pants from the medium surrounding him comprising pants being made from an elastical, liquid and gas proof and heat insulating material, said pants having legs with the lower portions of said pant legs being provided with inwardly folded cuffs made from a thin and pliable material such as rubber, wherein said cuffs are capable of forming a tight connection between the thighs of the wearer and said pants in the inwardly folded position of said cuffs, said pants having a waist portion having an inflatable zone extending all around said waist portion, an adjustable strap assembly, said strap assembly extending around said inflatable zone of said waist portion to press said inflatable zone of said pants against the waist of the wearer.

* * * * *